US010786540B2

(12) United States Patent
Mehta

(10) Patent No.: US 10,786,540 B2
(45) Date of Patent: *Sep. 29, 2020

(54) FORMULATIONS FOR THE TREATMENT OF MUCOSAL LESIONS

(71) Applicant: Raman Mehta, Kowloon (HK)

(72) Inventor: Raman Mehta, Kowloon (HK)

( * ) Notice: Subject to any disclaimer, the term of this patent is extended or adjusted under 35 U.S.C. 154(b) by 381 days.

This patent is subject to a terminal disclaimer.

(21) Appl. No.: 15/735,391

(22) PCT Filed: Jun. 10, 2016

(86) PCT No.: PCT/IB2016/000791
§ 371 (c)(1),
(2) Date: Dec. 11, 2017

(87) PCT Pub. No.: WO2016/198942
PCT Pub. Date: Dec. 15, 2016

(65) Prior Publication Data
US 2018/0104301 A1 Apr. 19, 2018

(30) Foreign Application Priority Data
Jun. 10, 2015 (EP) .................................. 15171355

(51) Int. Cl.
*A61K 36/9066* (2006.01)
*A61K 36/9068* (2006.01)
*A61K 36/185* (2006.01)
*A61K 9/00* (2006.01)
*A61K 9/06* (2006.01)
*A61P 1/02* (2006.01)

(52) U.S. Cl.
CPC .......... *A61K 36/9066* (2013.01); *A61K 9/006* (2013.01); *A61K 9/0056* (2013.01); *A61K 9/06* (2013.01); *A61K 36/185* (2013.01); *A61K 36/9068* (2013.01); *A61P 1/02* (2018.01); *A61K 2300/00* (2013.01)

(58) Field of Classification Search
None
See application file for complete search history.

(56) References Cited

U.S. PATENT DOCUMENTS

| 2006/0147989 | A1 | 7/2006 | Rosenbloom |
| 2009/0175971 | A1 | 7/2009 | Dreher |
| 2012/0107429 | A1 | 5/2012 | Lee et al. |
| 2018/0169175 | A1* | 6/2018 | Mehta ................ A61K 36/9066 |

FOREIGN PATENT DOCUMENTS

| CN | 102670588 A | 9/2012 |
| CN | 103638502 A | 3/2014 |
| CN | 104524508 A | 4/2015 |
| DE | 202009002126 U1 | 4/2009 |
| JP | 2004537575 A | 12/2004 |
| JP | 2013539770 A | 10/2013 |
| WO | 2004012655 A2 | 2/2004 |
| WO | 2011068812 A1 | 6/2011 |

OTHER PUBLICATIONS

JP2013001666A (English translation retrieved from https://worldwide.espacenet.com/). (Year: 2013).*
Ahmad et al., "Bioactive Compounds from Punica Granatum, Curcuma Longa and Zingiber Officinale and their Therapeutic Potential," Drugs of the Future, vol. 33, No. 4, Apr. 1, 2008, pp. 329-346.
Hiaghighi et al., "Pomegranate Juice may be a Potential Addition to Anti-Behcet Armamentarium: A Hypothesis," Clinical Rheumatology, vol. 26, No. 10, Apr. 4, 2007, pp. 1709-1710.
Database WPI, Week 201308, Thomson Scientific, XP-002748586, London, Jan. 7, 2013.
Database WPI, Week 201434, Thomson Scientific, XP-002748844, London, Mar. 19, 2014.
Database WPI, Week 201437, Thomson Scientific, XP-002748845, London, Apr. 2, 2014.
"Antiviral Potential of Selected Indian Medicinal (Ayurvedic) Plants Against Herpes Simplex Virus 1 and 2," North American Journal of Medical Sciences, Dec. 1, 2012, p. 641.
International Search Report issued on PCT/IB2016/000791 dated Aug. 18, 2016.
Soheil Z. Moghadamtousi et al., "A Review on Antibacterial, Antiviral, and Antifungal Activity of Curcumin," BioMed Research International, vol. 2014, 12 pages.

* cited by examiner

*Primary Examiner* — Michael Barker
(74) *Attorney, Agent, or Firm* — Carter, Deluca & Farrell LLP

(57) ABSTRACT

The present invention relates to formulations containing a combination of extracts from *Curcuma longa*, *Punica granatum* and *Zingiber officinale*, useful for the treatment and prevention of mucosal lesions, in particular those caused by Herpes virus or Behcet's syndrome. The formulations are especially effective in reducing the incidence of mucosal lesions of the mouth, throat and genital area.

14 Claims, No Drawings

FORMULATIONS FOR THE TREATMENT OF MUCOSAL LESIONS

CROSS REFERENCE TO RELATED APPLICATIONS

This application is a national stage application of International Application No. PCT/IB2016/000791, filed Jun. 10, 2016, which claims the benefit of and priority to European Patent Application No. 15171355.9, filed Jun. 10, 2015, the entire contents of each of which are hereby incorporated by reference herein.

STATE OF THE ART

Mucosal lesions are an important pathologic symptom of many diseases, causing significant distress to the affected patients. Mucosal lesions, in particular in the mouth or throat are among the most disturbing symptoms of Behcet's syndrome and of infections from viruses of the genus Herpesviridae (Herpes).

Behcet's syndrome, also called Behcet's disease, is a rare disorder that causes inflammation in blood vessels in the body. The signs and symptoms of Behcet's disease which may include mouth sores, eye inflammation skin rashes and lesions, and genital sores, vary from person to person and may come and go on their own. The exact cause of this syndrome is unknown, but it may be an autoimmune disorder, which means the body's immune system. Genetic and environmental factors may be responsible for Behcet's syndrome. This pathology is very rare in western countries but has a certain diffusion in Middle East and Asia. Diagnosis of Behcet's syndrome can take a long time, because the symptoms may come and go. For Behcet's syndrome there is no resolving cure, and the treatment is limited to antalgic products to reduce the pain. The difficulty to eradicate the disease bears the consequence that any treatments, either symptomatic or tentatively curative, must be protracted for very long time, sometimes even life-long, with the risk of toxicity due to accumulation of the drug in the organism. The publication Clin. Rheumatol., 2007, 26, 1709-1710 suggests, admittedly as a speculative a hypothesis, the use of pomegranate juice in the treatment of Behcet's disease: the speculation is based on the generic anti-inflammatory, antioxidant, antimicrobial activity known for the juice, with no indication, even of preliminary nature, of real efficacy against this disease. The two patent applications CN103638502 based on traditional Chinese medicine disclose the use, for treating Behcet's diseases, of mixtures of plant parts from 28 different species; they include inter alia ginger as a minority component of the mixture; this plant was chosen merely because of its spicy, hot, spleen, stomach, lung, warming effect. CN103690709, describes a traditional medicine used for Behcet's disease containing plant parts from 11 species, including Pseudodrynaria coronans, also popularly known as cliff ginger.

Herpesviridae are a genus of viruses responsible for important mucosal and dermatological disorders. The most common ones are herpes labialis from Herpes simplex HSV-1 virus, herpes genitalis from HSV-2 virus, herpes zoster from herpes virus 3 (HHV-3), herpes ohphthalmicus from any of viruses HSV-1, HSV2, HHV-3, herpes circinatus, herpes gestationis, etc. With respect to Herpes infections, a few antiviral compounds are currently used in therapy, in particular Acyclovir, some purine pseudometabolites, etc., however they have limited efficacy, often requiring prolonged treatments, and are not exempt from toxicity The narrow choice of available drugs represents a problem in case of patients being hypersensitive or non-responsive to the adopted treatment. The publication North American Journal of Medicinal Sciences, 2012, 4(12), 641, describes a primary screening study evaluating the effect of single plant extracts, inter alia *Punica granatum*, for activity against Herpes virus; in the same study, various plant extracts including *Curcuma longa* extract failed to exhibit anti-HSV potential. The patent applications US2006/0147989 and WO2004/012655 describe anti-herpes and antimicrobial compositions containing ginger and green tea as essential ingredients; further ingredients, e.g. turmeric and horseradish may be optionally present. None of the above documents discloses effects on the mucosal lesions caused by herpes virus: in fact standard anti-herpes treatments generally rely on "virucidal" activity, i.e. they inactivate the virus, but without specifically promoting healing of the damaged mucosa; the mucosa remains thus damaged for quite a long time after the treatment, being undesirably exposed to re-infection; healing of the mucosa depends on the mucosal self-regeneration capability, which is however slow when recovering from a viral attack; in summary, although known virucidal treatment may block the further development of the infection, the patient remains uncomfortably affected by the mucosal lesions, requiring long time to heal.

Extracts of various plants are further used in the treatment of a variety of disorders. For example, the patent publication JP2013001666 describes a nutrient composition for treating a conditions including atherosclerosis, cancer, cell damage, diabetes, cranial never disease, cerebral infarction, dementia, Parkinson's disease, alimentary mucosa disease, lung/broncus disorder, inflammation, menopausal disorder, rheumatism, atopic disease, containing inter alia, *Curcuma longa* extract, silylbum marianum seed, emblica officinale extract, wheat bran, Japanese tea leaf extract, sesame extract, pomegranate seed extract, ginger extract, soy isoflavone, withaniaroot, bacopa monnierileaf, etc. The utility model DE 20 2009 002 126 describes a nutritive composition useful for treating subjects under chemo-/radiotherapy: the composition contains a multitude of vitamins, minerals, carotenoids, omega-3-fatty acids, pomegranate extract and at least one extract chosen from broccoli, ginger and *curcuma*; in the exemplified compositions, the active ingredients of the present invention represent a minoritary part of the total active ingredients present. The patent application WO-A1-2011/068812 describes compositions for treating the oral cavity containing at least three extracts among *Punica granatum, Myristica fragrans, Zingiber officinale* and *Zizyphus joazeiro*, and an additional extract selected from another list of 38 plants; there is no specific disclosure of the combination on which the present invention is based. The publication Drugs of the Future, 2008, 33(4), pp. 329-346 describes separately the activities of *Punica granatum, Curcuma longa* or *Zingiber officinale*: the document refers the biochemical effects of these plants and their active components (antioxidant, anti-inflammatory, antimicrobial, anticancer, antimutagenic), with no suggestion or teaching on how to optimize their activities; the document does not suggest any specific combination of these agents, nor it prospects a possible synergism among them.

The need is therefore present to increase the number of drugs available to treat mucosal lesions. A need is particularly felt to treat/prevent the mucosal lesions in the mouth and/or throat, especially those associated to Herpes infections or Behcet's syndrome. It is particularly desired to respond to such needs with new medicaments having low toxicity for the patient, thus being suitable for repeated, chronic or even life-long treatments.

SUMMARY

It has now been discovered that a combination of extracts of *Curcuma longa, Punica granatum* and *Zingiber officinale* displays a strong activity on mucosal lesions. Object of the invention is the aforesaid combination of extracts, the relevant pharmaceutical compositions, methods of preparation, and use thereof in the treatment/prevention of mucosal lesions. The invention further comprises the aforesaid combination of extracts for use in the treatment/prevention of mucosal lesions, and the corresponding methods of treatment.

DETAILED DESCRIPTION OF THE INVENTION

*Curcuma longa* is the botanic name of turmeric. *Punica granatum* is the botanic name of pomegranate. *Zingiber officinale* is the botanic name of ginger. For each of these plants, the botanic and common name are used herein indifferently.

Throughout this description and claims, whenever weight (or weight percent) amounts of extracts are disclosed, they are always meant as "dry" extracts, i.e. considering only the weight of the non-liquid ingredients of the extract; likewise, whenever weight (or weight percent) amounts of specific ingredients within an extract are disclosed, they are always calculated by reference to the extract in "dry" form.

Nevertheless, the combinations/formulations/pharmaceutical compositions/uses objects of the present invention are not limited to using dried extracts, but extend also to using liquid and fluid extracts. Any types of extracts can be used herein, indifferently from their specific method of extraction and their physical status.

*Curcuma longa* extracts are usually obtained from roots and rhizomes of the plant. They contain curcuminoids in association with other plant components working as natural vehicles. Total alcoholic extracts are preferably used; they can be prepared e.g. according the modalities of Ayurveda system of medicine (Turmeric extract), by extraction of *Curcuma* rhyzomes with ethanol; they typically contain 20-30% wt curcuminoids, preferably 25% wt., referred to the dry extract.

*Punica granatum* extracts are typically obtained from the whole fruit. They have a polyphenol content generally ranging from 60 to 95% wt., preferably 75%; ellagic acid and polymers thereof (punicalgines) are the main active components of the extract: they are normally present in the extract in a minimum amount of 30% wt, preferably more than 40% wt., referred to the dried extract. In a preferred embodiment, the extract can be prepared by extracting the whole fruits with mixtures of ethanol/water or acetone, concentrating the extracts to water and purifying the aqueous solution, after elimination of insoluble material, through absorption of polyphenos on a polystirenic resin; the polyphenols are recovered from the resin by elution with ethanol and then concentrated to dryness.

*Zingiber officinale* extract is usually obtained from rhizomes. It is preferably a lipophilic extract; it contains from 20 to 50% of a mixture of gingerols+shoagols, referred to the dried extract. In a preferred embodiment, it is obtained by extraction of the dried rhizomes with n-Hexane or with $CO_2$ in supercritical condition at a temperature of 45° C. and a pressure of 220 bars.

In one embodiment of the invention, the three aforementioned extracts are the sole active agents used (this does not preclude the joint use of non-active agents, i.e. vehicles and formulation excipients, including those possibly having a pharmaceutical effect as a side activity: the latter may still be used in modes/amounts conform to their role as vehicle/excipient).

Alternatively, additional active agents may be used, but on condition that the combination of extracts of the invention remains prevalent, i.e:

said combination of *Curcuma longa, Punica granatum* and *Zingiber officinale* accounts for more than 50% (or, preferably, more than 75%, 85%, 90%, 95% or 99%) by weight of the total active agents present and/or any possible active agent additional to said *Curcuma longa, Punica granatum* and *Zingiber officinale* is present in an amount at least 50% by weight lower than the lowest among said *Curcuma longa, Punica granatum* and *Zingiber officinale*: accordingly a combination of, for example, 60 mg turmeric extract, 20 mg pomegranate extract and 10 mg ginger extract, will allow the presence of additional active agents, each one being present in amounts of 5 mg or lower.

Further in the invention, *Curcuma Longa* is generally present in higher concentrations compared to the two other members, i.e. *Zingiber officinale* and *Punica granatum*, i.e. the weight ratio among these three active agents, based on their dried extracts, is: $6(\pm 2):2(\pm 1):1(\pm 0.5)$, where the data in parenthesis represent possible ±weight ratio variations for each component.

According to another preferred embodiment, the formulations contain the three extracts within the following weight intervals, per dosage unit, referred to dried extracts:

| | |
|---|---|
| *Curcuma longa* extract: | 20 to 100 mg, |
| *Punica granatum* extract (ctg. 40% ellagic acid deriv.) | 10 to 60 mg |
| *Zingiber officinale* extract (ctg. 35% gingerols): | 2 to 20 mg |

According to a more preferred embodiment the content per dosage unit, referred to dried extracts, is:

| | |
|---|---|
| *Curcuma longa* extract: | 50 mg, |
| *Punica granatum* extract (ctg. 40% ellagic acid deriv.) | 20 mg |
| *Zingiber officinale* extract (ctg. 35% gingerols): | 10 mg |

A further preferred embodiment concerns the topical gel formulation described in example 1 of this application, or the orodispersible mucoadhesive tablet described in example 2 of this application, or the slow release formulation tablet described in example 3 of this application, wherein the weight of each of the formulation ingredients can vary within a range of ±15%.

Most preferably, the combination of the present invention is formulated as a buccal composition, i.e. for local application in the buccal cavity, capable to release the active principles during a prolonged time after application, typically formulated as an orodispersible tablet or film (preferably mucoadhesive); alternatively the combination is formulated as inhalatory composition, e.g. as aerosol, spray, etc. In particular the inventors have unexpectedly found that the present combination of extracts, after a suitable time of permanence in the buccal cavity ensures an increase in the amount of salivar lysozyme, an enzyme involved in capturing/inactivating possible environmental contaminants entering in the mouth such as bacteria and viruses. Even more surprisingly, the found increase was unrelated to enhanced salivation, i.e. it consisted in an enhanced saliva concentration of lysozyme, thus independent from the amount of secreted saliva. The present combination is thus unexpectedly effective when formulated as a buccal sustained release composition, exerting a very effective preventive effect against bacterial of viral infection such as common flu. The critical importance of an effective preventive treatment for these diseases is immediately evident, considering their widespread diffusion, their social impact and the length of curative therapies once infection has taken place, often involving the undesirable use of antibiotic drugs.

The present compositions were found particularly effective in that they not only prevented and/or inhibited the development of the infections causing mucosal lesions: they also promoted the healing of the damaged mucosa, such that a complete recovery from the lesions could be obtained within a short treatment period involving both the elimination of the virus and the cure of its mucosal damages: an "integrated" antiviral treatment is thus provided, with a higher patient's satisfaction who can return more quickly to his/her physiological pre-infection status.

In a further preferred embodiment, the mucosal lesions treatable by the combination of extracts of the present invention are those resulting from mucositis induced by chemo- or radiotherapy; accordingly the combination is also used for treating or preventing mucositis induced by chemo- or radiotherapy.

The combination of extracts of the invention, although being effective as such, is generally formulated and provided to the patient in a conventional delivery form, preferably for local administration on the affected mucosa; in particular, in case of mouth lesions, the administration is locally applied to the mouth area concerned (lips, gum, palate, throat, etc.); preferred local administration forms are gels, creams, powders, solutions; systemic administration is also possible and can be effected via any conventional route: oral, intramuscular, intravenous, transdermal, rectal, etc.; preferred systemic administration forms are the oral ones, in particular solutions, tablets, capsules, granules, pellets, gummy lozenges, chewing gum etc.; some preferred forms are those formulated for a slow/controlled release; other preferred forms are tablets capable to form gels once in contact with water, so as to ease administration in patients with difficulties to swallow solid bodies, e.g. babies and elderly. All the above delivery forms can be prepared according to conventional methods as reported in standard books of pharmaceutical technology.

The combination and formulations of the invention is herein used to treat mucosal lesions of any origin. It is particularly effective on mouth, throat or genital lesions, more particularly those occurring in case of Herpes virus infections (Herpes simplex virus HSV-1, HSV-2, HHV-3, Herpes zoster virus) thus being useful to treat herpes labialis, herpes genitalis, herpes zostes, herpes ophptalmicus, herpes circinatus, herpes gestationis, or those occurring in Behcet's syndrome. The combinations and formulations of the invention are most active on lesions of the mouth (herein meant to include lips) and/or genital area.

The present combination and formulations also display a parallel antibacterial activity which usefully complements the present treatments by preventing any possible bacterial complications (e.g. *Candida albicans*) associated to mucosal lesions.

The combination and formulations also achieved a strong enhancement of lysozyme levels in the saliva, up to 5 times the levels in healthy subjects: since lysozyme is involved in the lysis of virus, bacteria and other xenobiotics, this complementary effect further enhances the immunoprotective properties of the saliva, strengthening the immunoresistance of the mucosa of the mouth and neighbouring areas against (further) infections. The present combination and formulations were also found to build a temporary protective layer upon the contacted mucosas, thus further increasing their resistance against pathogenic agents present in the atmosphere.

The daily dosage at which the present combination is administered can widely vary in function of the patient conditions, administration route, and type and severity of the disease to be treated. Said daily dosage can be taken via a single administration or, preferably, subdivided in repeated administrations throughout the day, e.g. 3 times a day. The treatment is effective almost immediately: however prolongation of the treatment over a minimum of 2-3 days, preferably for 1 or 2 weeks, is advised to obtain a significant and consistent inhibition of the symptoms. The composition, based on a combinations of natural extracts, was found highly tolerable and with no side effects reported by the treated patients.

The invention is now described by means of the following non-limitative examples.

EXAMPLES

Example 1 Topical Gel

| | |
|---|---:|
| *Curcuma longa* alcoholic extract (turmeric) or other species | 500 mg |
| *Punica granatum* extract 40% ellagic acid der | 120 mg |
| *Zingiber officinale* lipophilic extract | 200 mg |
| Hydroxyethylcellulose | 3000 mg |
| Polysorbate 80 | 3000 mg |
| p-hydroxy-methylbenzoate | 100 mg |
| Propylene glycol | to 100000 mg |

Example 2 Orodispersible Mucoadhesive Tablets

| | |
|---|---:|
| *Curcuma longa* alcoholic extract (turmeric) or other species | 50 mg, |
| *Punica granatum* extract 40% ellagic acid der | 20 mg |
| *Zingiber officinale* lipophilic extract | 10 mg |
| Alginic acid Sodium salt | 200 mg |
| Xylitol | 600 mg |
| Ammonium glycirrizinate | 10 mg |
| Sodium Cyclamate | 40 mg |
| Polisorbate 80 | 5 mg |

Example 3 Slow Release Formulation Tablet

| | |
|---|---:|
| *Curcuma longa* alcoholic extract (turmeric) or other species | 50 mg, |
| *Punica granatum* extract 40% ellagic acid der.: | 20 mg |
| *Zingiber officinale* lipophilic extract 35% gingerols: | 8 mg |
| Xylitol: | 430 mg |
| Hyaluronic acid: | 200 mg |
| Ammonium glycirrizinate | 10 mg |
| Sodium Cyclamate | 40 mg |
| Polysorbate 80 | 5 mg |

Example 4 Clinical Studies

The main targets of the clinical studies were:
a—the cicatrization time of the lesions in Behcet's diseases in the mouth.
b—the reduction of signs/symptoms—
c—the reduction of days of Herpetic diseases
d—Determination of saliva and lysozyme content.

Herpes Treatment 6 female subjects with Herpes labialis (age 18-26) were administered the formulations described in example 2; the tablet was administered 4 times daily (allowing to slowly dissolve in the mouth) for 1 week. Further patients were administered with the topical gel of example 1; the gel was applied on the lesions for the period necessary for the elimination of the symptoms and recovery of the normal patients situation.

The results data, tolerability and possible adverse effects were monitored in a daily diary every day and for 7 days after the end of the period of administration of the supplement.

Soon after beginning of the treatment the herpetic lesions decreased rapidly and disappeared in an average of 4.4 days; in the placebo group, the lesions persisted at 8 days.

Bechet's Disease Treatment

In case of Behcet's disease, 5 patients were treated with the gel formulation of example 1 for 5 times/day for two weeks; a decrease in the number of ulcerations (9 to 3) along with a decrease in the size of ulceration (76%) and reduction of pain (46%) were observed.

On another group of patients, treated with the formulation of example 3, the lysozyme concentration in the saliva was evaluated before the first administration (controls), and after 1 week of treatment (3 tablets/daily). The results are reported in table 1.

TABLE 1

Mean values for lysozyme concentration (micrograms/ml, turbidimetric assay) in centrifuged saliva. Patient population: 10 male subjects/age range 35-55 yrs, mean 42.32; 3.4 yrs

| Patient no. | Lysozyme before administration | 1 week after administration |
| --- | --- | --- |
| 01 | 2.3 | 2.9 |
| 02 | 2.3 | 7.5 |
| 03 | 2.4 | 12.3 |
| 04 | 2.1 | 11.2 |
| 05 | 2.0 | 12.1 |
| 06 | 2.3 | 11.4 |
| 07 | 2.4 | 12.0 |
| 08 | 2.2 | 11.8 |
| 09 | 2.4 | 13.0 |
| 10 | 2.2 | 11.4 |

The invention claimed is:

1. A method of preventing and/or treating mucosal lesions, comprising administering to a patient in need thereof, a combination of active agents consisting of extracts of *Curcuma longa, Punica granatum* and *Zingiber officinale*, the extracts of *Curcuma longa, Punica granatum* and *Zingiber officinale* being present in the respective weight ratios 6(±2):2(±1):1(±0.5).

2. A method of preventing and/or treating mucosal lesions, comprising administering to a patient in need thereof, a combination of active agents comprising extracts of *Curcuma longa, Punica granatum* and *Zingiber officinale*, the extracts of *Curcuma longa, Punica granatum* and *Zingiber officinale* being present in the respective weight ratios 6(±2):2(±1):1(±0.5),
wherein the extracts represent overall more than 50% by weight of the total administered active agents, and/or
wherein each possible active agent additional to the extracts is present in an amount at least 50% by weight lower than the lowest among the extracts of *Curcuma longa, Punica granatum* and *Zingiber officinale*.

3. The method according to claim 2, wherein the extracts of *Curcuma longa, Punica granatum* and *Zingiber officinale* represent overall more than 90% by weight of the total administered active agents.

4. The method according to claim 1, wherein the extract of *Curcuma longa* contains curcuminoids in an amount from 20% to 30% by weight, the extract of *Punica granatum* contains polyphenols in an amount from 60% to 95% by weight, and the extract of *Zingiber officinale* contains a total of gingerols and shogaols in an amount from 20% to 50% by weight.

5. The method according to claim 1, wherein the combination is formulated as a unit dose of administration, comprising: 20-100 mg of *Curcuma longa* extract, 10-50 mg of *Punica granatum* extract and 2-20 mg *Ginger officinale* extract.

6. The method according to claim 1, wherein the combination is formulated with pharmaceutical excipients.

7. The method according to claim 1, wherein the combination is in a form suitable for local or systemic administration.

8. The method according to claim 1, wherein mucosal lesions to be treated are present in the mouth, lips, throat and/or genital area.

9. The method according to claim 1, wherein the mucosal lesions are consequential to an Herpesviridae infection or to Behcet's disease.

10. The method according to claim 9, wherein the mucosal lesions are consequential to herpes labialis, herpes gentialis, herpes zoster, herpes ophthalmicus, herpes circinatus, herpes gestationis.

11. The method according to claim 9, wherein the Herpesviridae is one or more among HSV-1, HSV-2, HHV3, HZV.

12. The method according to claim 1, wherein the mucosal lesions are consequential to chemo- and/or radio-therapy.

13. The method according to claim 1, wherein the combination is configured for treating and/or preventing bacterial complications on the affected mucosas.

14. The method according to claim 1, wherein the combination is configured for enhancing lysis of xenobiotics via contact of the combination with the saliva.

* * * * *